(12) United States Patent
Satake

(10) Patent No.: US 9,241,623 B2
(45) Date of Patent: Jan. 26, 2016

(54) OCULAR AXIAL LENGTH MEASUREMENT APPARATUS

(75) Inventor: Miyuki Satake, Gamagori (JP)

(73) Assignee: NIDEK CO., LTD., Aichi (JP)

( * ) Notice: Subject to any disclaimer, the term of this patent is extended or adjusted under 35 U.S.C. 154(b) by 72 days.

(21) Appl. No.: 14/129,393

(22) PCT Filed: Jun. 28, 2012

(86) PCT No.: PCT/JP2012/066549
§ 371 (c)(1),
(2), (4) Date: Mar. 24, 2014

(87) PCT Pub. No.: WO2013/002332
PCT Pub. Date: Jan. 3, 2013

(65) Prior Publication Data
US 2014/0333895 A1 Nov. 13, 2014

(30) Foreign Application Priority Data
Jun. 29, 2011 (JP) .................................. 2011-144497

(51) Int. Cl.
*A61B 3/14* (2006.01)
*A61B 3/00* (2006.01)
(Continued)

(52) U.S. Cl.
CPC ................. *A61B 3/1005* (2013.01); *A61B 3/14* (2013.01); *A61B 8/10* (2013.01); *A61B 3/0075* (2013.01); *A61B 3/0083* (2013.01); *A61B 3/102* (2013.01); *A61B 3/152* (2013.01)

(58) Field of Classification Search
CPC .......... A61B 3/103; A61B 3/152; A61B 3/14; A61B 3/113; A61B 3/1225; A61B 3/024; A61B 19/5244; A61N 7/00
USPC ......... 351/208, 200, 205, 206, 210, 221, 222, 351/246, 207, 209; 600/407; 601/2
See application file for complete search history.

(56) References Cited

U.S. PATENT DOCUMENTS

2006/0084856 A1* 4/2006 Biggins et al. ................ 600/399
2006/0241437 A1* 10/2006 Phillips et al. ................ 600/438
(Continued)

FOREIGN PATENT DOCUMENTS

EP 1938744 7/2008
JP 2005-131249 5/2005
(Continued)

OTHER PUBLICATIONS

International Search Report dated Jul. 24, 2012 filed in PCT/JP2012/066549.

*Primary Examiner* — Dawayne A Pinkney
(74) *Attorney, Agent, or Firm* — Rankin, Hill & Clark LLP

(57) ABSTRACT

An ocular axial length measurement apparatus is provided with: a measurement section for obtaining the ocular axial length of an examinee's eye by using an optical interferometer; a drive mechanism for adjusting the relative positions of the measurement section and the examinee's eye; an operation section operated by an examiner; and a control unit. The ocular axial length measurement apparatus is equipped with an ultrasonic probe for obtaining length information in an axial direction of the examinee's eye in advance, or configured to mount the ultrasonic probe. The control unit, when measuring the eye using the ultrasonic probe, changes a setting at the time of measuring the eye using the ultrasonic probe based on an operation signal output from the operation section.

17 Claims, 3 Drawing Sheets

(51) Int. Cl.
*A61B 3/10* (2006.01)
*A61B 8/10* (2006.01)
*A61B 3/15* (2006.01)

(56) References Cited

U.S. PATENT DOCUMENTS

2008/0151188 A1   6/2008   Kawai

2010/0198074 A1*   8/2010   Satake .................. 600/449

FOREIGN PATENT DOCUMENTS

| | | |
|---|---|---|
| JP | 2008-029468 | 2/2008 |
| JP | 2008-161218 | 7/2008 |
| JP | 2011-097998 | 5/2011 |

* cited by examiner

OCULAR AXIAL LENGTH MEASUREMENT APPARATUS

TECHNICAL FIELD

The present apparatus relates to an apparatus for measuring the ocular axial length of an examinee's eye.

BACKGROUND ART

As ocular axial length measurement apparatuses, an apparatus for measuring an ocular axial length with an optical interferometer and an apparatus for measuring an ocular axial length with an ultrasonic probe are known.

There is a known combo apparatus in which a device for measuring an ocular axial length with an optical interferometer is provided with an ultrasonic probe. Thus, the combo apparatus uses ultrasonic waves to measure an optical interferometer. (see Patent Document 1).

PRIOR ART DOCUMENT

Patent Document

Patent Document 1: JP-A-2008-161218

SUMMARY OF THE INVENTION

Problems to be Solved by the Invention

In the measurement of an ocular axial length using an ultrasonic probe, the gain of a reception signal, and the gate position of a reception waveform are adjusted. In the measurement of a corneal thickness with an ultrasonic probe, the results of measurements at a plurality of positions on the cornea are successively plotted.

However, compared with the dedicated apparatus for measuring an ocular axial length with an ultrasonic probe, the combo apparatus may cause a decrease in operability or may lead to a complicated operation system.

In view of the above problem, a technical object of the present invention is to enable an examiner to easily perform ultrasonic measurement even in the case of the optical interference/ultrasonic combo apparatus.

Solutions to the Problems

In order to achieve the object, the characteristic features of the present invention are as follows:

(1)

An ocular axial length measurement apparatus includes; a measurement unit including a measuring optical system with an optical interferometer for optically measuring the ocular axial, length, of an examinee's eye in a contactless manner, and an imaging optical system for capturing an anterior segment observation image; a drive mechanism for adjusting the relative positions of the measurement unit and the examinee's eye; an operation section operated by an examiner so as to drive the drive mechanism or the measurement unit; a monitor capable of displaying the anterior segment observation image; and a controller that controls the measurement unit and the driving of the drive mechanism based on an operation signal output from the operation section, wherein the controller, in a state in which an ultrasonic probe for obtaining length information in an axial direction of the examinee's eye is mounted in advance or attached via a cable, changes a setting at the time of measuring the examinee's eye by controlling the ultrasonic probe based on the operation signal input from the operation section.

(2)

The ocular axial length measurement apparatus according to (1), wherein the drive mechanism includes a first, drive mechanism for driving the measurement unit in a vertical direction; and the operation section is a rotating knob operated by the examiner to drive the measurement unit in the vertical direction by the first drive mechanism.

(3)

The ocular axial length measurement apparatus according to (2), wherein the ultrasonic probe is an ultrasonic probe for A-mode; and the controller displays on the monitor both a reception waveform of an echo signal detected by the ultrasonic probe and a gate target indicating a gate position corresponding to a predetermined site with respect to the reception waveform, and the controller adjusts the gate position with respect to the reception waveform based on the operation signal input from the rotating knob.

(4)

The ocular axial length measurement apparatus according to any one of (2) and (3), wherein the controller modifies a gate position on the monitor based on the operation signal input from the rotating knob; and the controller identifies the echo signal corresponding to the predetermined site based on the modified gate position.

(5)

The ocular axial length measurement apparatus according to any one of (2) to (4), wherein the ultrasonic probe is an ultrasonic probe for a pachymetry mode; and the controller displays on the monitor both a map indicating a plurality of measurement points on the cornea and a selection display indicating a current measurement position on the map, and the controller modifies the position of the selection display on the map based on the operation signal input from the rotating knob.

(6)

The ocular axial length measurement apparatus according to my one of (1) to (5), wherein the drive mechanism includes a second drive mechanism for driving a chin rest in the vertical direction; and the operation section is a chin rest switch operated by the examiner to drive the chin rest in the vertical direction by the second drive mechanism.

(7)

The ocular axial length measurement apparatus according to any one of (1) to (6), wherein the ultrasonic probe is an ultrasonic probe for A-mode; and the controller displays on the monitor both a reception waveform of an echo signal detected by the ultrasonic probe and a gate target indicating a gate position corresponding to a predetermined site with respect to the reception waveform, and the controller adjusts the gain of a signal detected by the ultrasonic probe based on an operation signal input from the chin rest switch.

(8)

The ocular axial length measurement apparatus according to any one of (1) to (7), wherein the ultrasonic probe is an ultrasonic probe for a pachymetry mode; and the controller displays on the monitor both a map indicating a plurality of measurement points on the cornea and a selection display indicating a current measurement position on the map, and the controller adjusts the gain of a signal detected by the ultrasonic probe based on an operation signal input from the chin rest switch.

(9)

The ocular axial length measurement apparatus according to any one of (1) to (8) including a measurement start switch operated by the examiner to input a trigger signal for starting measuring in the measurement unit, wherein the controller starts transmission and reception of ultrasonic waves by the ultrasonic probe in response to the trigger signal input from the measurement start switch.

(10)

The ocular axial length measurement apparatus according to any one of (1) to (9) including a start switch operated by the examiner to input a trigger signal for starting measuring in the measurement unit, wherein the controller, after the start of transmission and reception of ultrasonic waves, acquires length information based on a signal detected by the ultrasonic probe in response to the trigger signal input from the start switch; and the controller displays the acquired length information on the monitor.

(11)

The ocular axial length measurement apparatus according to any one of (1) to (10), wherein, the monitor includes a touchscreen; and the controller adjusts a gate position with respect to a reception waveform based on an operation signal input from the touchscreen.

(12)

The ocular axial length measurement apparatus according to my one of (1) to (11), wherein, the monitor includes a touchscreen; and the controller adjusts the gain of a signal detected by the ultrasonic probe based on an operation signal input from the touchscreen.

(13)

The ocular axial, length measurement apparatus according to any one of (1) to (12), wherein the monitor includes a touchscreen; and the controller, on the basis of an operation signal input from the touchscreen, modifies the position of a selection display on a map and adjusts the gain of a signal detected by the ultrasonic probe.

(14)

The ocular axial length measurement apparatus according to any one of (7) to (13), wherein the controller displays a numerical value of the adjusted gain on the monitor.

Effects of the Invention

In view of the problem, the present invention enables the examiner to easily perform an ultrasonic measurement even, with an optical interference/ultrasonic combo apparatus.

DESCRIPTION OF EMBODIMENTS

An apparatus according to an embodiment will be described with reference to the drawings. FIG. 1 is a diagram illustrating an exterior configuration of an ocular axial length measurement apparatus according to the embodiment. FIG. 2 is a control block diagram illustrating the ocular axial length measurement apparatus according to the present embodiment.

A main body section 10 of the apparatus according to the present embodiment includes a base 1, a lace support unit 2, a measurement unit (measurement section) 4, a joystick 5; an up/down switch 6, a first drive section 7, a second drive section 8, and a monitor 9. The face support unit 2 is attached to the base 1 and includes a chin rest 2a and a forehead rest 2b. The first drive section 7 includes a mechanism for moving the measurement unit 4 in X, Y, and Z directions relative to the examinee's eye. The first drive section 7 employs, for example, a drive mechanism that mechanically drives the measurement unit 4, a drive mechanism that drives the measurement unit 4 by motor drive, or a combination of these mechanisms. The second drive section 8 includes a mechanism with a motor for moving the chin rest 2a op and down by motor drive.

The first drive section 7 and the second drive section 8 are used as a drive mechanism for adjusting the relative positions of the measurement unit 4 and an eye E. For the detailed configuration of the first drive section 7 and the second drive section 8, for example, reference may be made to JP-A-2004-174155.

The measurement unit 4 contains a measuring optical system 4a. The measuring optical system 4a includes a light source, an optical interferometer, and a light receiving device, and optically measures the ocular axial length in a contactless manner. The optical interferometer guides, for example, light from the light source to the eye E, and then adjusts the optical path length. In this way, the optical interferometer causes reflected light from the fundus to interfere with reflected light from the cornea. The optical interferometer causes the resultant light (interference light) to be received by the light receiving device. The members of the measuring optical system 4a are connected to a control section 80. The control section 80 measures the ocular axial length based on an interference signal output from the light receiving device. For the detailed configuration and operation of the measuring optical system 4a, JP-A-2010-184048 may be referenced. The present apparatus is configured such that an examinee and an examiner face each other with the main body section 10 disposed in between.

The joystick 5 is operated by the examiner. The up/down switch 6 is disposed on, for example, the examiner side of the main body section 10. The joystick 5 may include a mechanical mechanism or an electric mechanism. The first drive section 7 moves the measurement unit 4 to the front, rear, left, or right in response to a tilting operation of the joystick 5.

The joystick 5 includes a rotating knob 5a and a measurement start switch 5b. The rotating knob 5a includes a rotary detector (such as a rotary encoder), and detects a rotation signal (such as the rotation speed or amount) of the rotating knob. The first drive section 7 moves the measurement unit 4 up or down in response to the rotating operation of the rotating knob 5a.

The rotating knob 5a is used as an operation section operated by the examiner to drive the first drive section 7 by manual operation. The measurement start switch 5b is used as an operation section operated by the examiner to input a trigger signal for starting measuring in the measurement unit 4.

The up/down switch 6 is operated by the examiner. The up/down switch 6 is disposed, for example, on the examiner side of the main body section 10. The up/down switch 6 includes an UP switch 6a for driving the chin rest 2a upward, and a DOWN switch 6b for driving the chin rest 2b downward. The second drive section 8 moves the chin rest 2a up or down in response to the operation of the up/down switch 6.

The up/down switch 6 is used as an operation section manually operated by the examiner to drive the second drive section 8 by manual operation.

The monitor 9 is a touchscreen-attached monitor and displays an anterior segment observation image, measurement results, measurement parameters, and the like. The monitor 9 is disposed, for example, on the examiner side of the main body section 10.

The control section 80 measures the ocular axial length by controlling the measurement unit 4. The control section 80 also controls the driving of the drive mechanism (such as the first drive section 7 and the second drive section 8) based on an operation signal output from the operation section (such as the rotating knob 5a, the measurement start switch 5b, or the up/down switch 6).

The present apparatus is equipped with an ultrasonic probe 302 in advance, or is configured to mount the ultrasonic probe 302. The ultrasonic probe 302 is used as a device for obtaining length information of the eye E in the axial direction. The ultrasonic probe 302 (see FIG. 2) is an ultrasonic probe for A-mode or pachymetry mode and includes a transducer 312. The ultrasonic probe 302 is used to measure the ocular axial length by ultrasonic waves. The ultrasonic probe 302 is configured to be held by the examiner and connected to the main body section 10 via a cable, for example.

Intensity data of an echo signal acquired by the ultrasonic probe 302 is detected as an ultrasonic signal. The control section 80 controls the driving of a clock generation circuit 311. The control, section 80 causes ultrasonic waves to be transmitted from the transducer 312 via a transmitter 317 (wave transmission). Reflected echo from the eye tissues is received by the transducer 312 (wave reception), and converted by an A/D converter 313 into a digital signal via an amplifier 318. The reflected echo information in the form of digital signal is stored in the sampling memory 316. The control section 80 generates measurement data based on the echo information stored in the sampling memory 316, and displays the measurement data on the monitor 9.

A configuration of the control system will be described. For example, the control section 80 controls the apparatus as a whole and calculates measurement values. The control section 80 is connected to each of the various members of the measurement unit 4, the ultrasonic probe 302, the monitor 9, the first drive section 7, the second drive section 8, the memory 85, the rotating knob 5a, the measurement start switch 5b, the up/down switch 6, and a foot switch 400.

The present apparatus is configured such that the measurement mode can be automatically or manually switched. The present apparatus may be set to a first measurement mode or a second measurement mode. The first measurement mode is an optical interference measurement mode in which the axial direction length of the eye is measured using the measurement unit 4a. The second measurement mode is an ultrasonic measurement mode in which the axial direction length of the eye is measured by using the ultrasonic probe 302. A mode switch (such as a mode changeover switch or the control section 70) is disposed on the touchscreen of the monitor 9 or the main body section 20.

Optical Interference Measurement Mode

First Measurement Mode

In the following, an example of the operation of the present apparatus will be described. The present apparatus is set to the first measurement mode as the initial, setting. The examinee's face is supported by the face support unit 2. The examiner operates the up/down switch 6 in order to adjust the height of the chin rest 2a to the examinee. The control section 80 controls the driving of the second drive section 8 based on the operation signal from the up/down switch 6 to drive the chin rest 2a upward or downward.

The monitor 9 displays an anterior segment image of the eye E captured by an anterior segment imaging optical system (not shown). The examiner observes the anterior segment image on the monitor 9. The examiner, in order to align the optical axis of the measuring optical system 4a with the eye E, operates the joystick 5 and the rotating knob 5a. The control section 80 drives the measurement unit 4 upward or downward by controlling the driving of the first drive section 8 based on the operation signal from the rotating knob 5a. When the joystick 5 is an electric joystick, the control section 80 drives the measurement unit 4 in the front, rear, left, or right direction by controlling the driving of the first drive section 8.

Alter alignment is completed, the examiner presses the measurement start switch 5b. The control section 80, using the operation signal from the switch 5b as a trigger, starts measuring the ocular axial length. The control section 80, after causing the light, source of the measuring optical system 4a to emit light, adjusts the optical path length of the interferometer of the measuring optical system 4a. As a result of the optical path length adjustment, the control section 80 obtains an ocular axial length value of the eye E based on the interference signal detected by the light receiving device. The control section 80 displays the measurement result on the monitor 9.

When the eye E is a severely cataract eye, the measurement light is blocked (scattered) by the opaque portion. As a result, the scattered light enters the light receiving device, whereby deterioration of measurement accuracy is caused. As a countermeasure, the examiner measures the ocular axial length in the second measurement mode in which the ultrasonic probe 302 is used.

Ultrasonic Measurement Mode

Second Measurement Mode

The apparatus according to the present embodiment includes, as the second measurement mode, an ocular axial length measurement mode (A-mode) and corneal thickness measurement mode (pachymetry mode), and operates in response to each set mode. The ultrasonic probe 302 is prepared for each measurement mode and connected to the main body section 10 as needed.

The ultrasonic measurement is performed with the examinee's face fixed on a face support unit (a configuration separate from the face support unit 2) installed on the right or left side of the main body section 1. The face support unit is attached to an electric optical base.

When the eye is measured by using the ultrasonic probe 302, the control section 80 modifies the setting at the time of measuring the eye by using the ultrasonic probe 302 on the basis of the operation signals output from the operation sections used for the measuring in the first measurement mode (such as the rotating knob 5a, the measurement start switch 5b, or the up/down switch 6).

In the following, an example of operation in the ocular axial length measurement mode will be described. FIG. 3 illustrates an example of the display screen in the ocular axial length measurement mode. Generally, the control section 80 controls the apparatus as a whole so that the operation signal from the up/down switch 6 can be utilised for adjusting the gain of an echo signal. The control section 80 controls the apparatus as a whole so that the operation signal front the rotating knob 5a can be used for moving the retinal detection gate. The control section 80 controls the apparatus as a whole so that the operation signal from the measurement start switch 5b can be utilized for starting the transmission and reception of ultrasonic waves by the ultrasonic probe 302, and acquiring a measurement value.

For example, when the ocular axial length is measured by using the ultrasonic probe 302, the control section 80 displays a reception waveform W detected by the ultrasonic probe 302 and a gate target G indicating the gate position corresponding to a predetermined site on the monitor 9. The control section 80, on the basis of the operation signal input from the rotating knob 5a, adjusts the gate position with respect to the reception waveform. The control section 80, on the basis of the operation signal input from the up/down switch 6, adjusts the gain of the signal detected by the ultrasonic probe 302.

For example, the control section 80 starts transmission and reception of ultrasonic waves by the ultrasonic probe 302 in response to the operation signal from the measurement start switch 5b. The control section 80, in response to the operation signal from the measurement start switch 5b after the start of transmission and reception of ultrasonic waves, acquires length information based on the signal detected by the ultrasonic probe 302, and displays the acquired length information on the monitor.

First, the examiner numbs the eye E with anesthetic eye drops. The examiner, while holding the probe 302 with one hand, contacts the end of the probe 302 onto the cornea. Also, the examiner, using the other hand, operates the rotating knob 5a, the measurement start switch 5b, or the up/down switch 6.

The examiner contacts the end of the probe 302 onto the eye E. Then, the examiner presses the measurement start switch 5b in order to obtain an echo signal from the eye E. The control section 80 controls the operation of the probe 302 by using the signal from the measurement start switch 5b as a trigger. The control section 80, in order to receive a reflected wave from the eye E with the transducer 312, irradiates the eye E with ultrasonic waves from the transducer 312.

The control section 80 displays the waveform of the echo signal detected by the probe 302 (A-mode waveform W) on the monitor 9 (see FIG. 3). In the A-mode waveform W, the left side corresponds to the cornea side, and the right side corresponds to the fundus side. On the monitor 9, a currently set gain is displayed as a value. The value is increased or decreased depending on the increase or decrease in gain. A dotted-line mark G displayed along with the A-mode waveform W is a target indicating the detection gate for the retinal echo. The display position of the dotted-line mark G is adjusted by the control section 80.

Gain Adjustment

The examiner, in order to obtain, a desired waveform, operates the up/down switch 6 while adjusting the position and angle of the probe 302. When the amplitude of the A-mode waveform W is smaller than an allowable level, the examiner operates the UP switch 6a. The control section 80 increases the gain in the amplifier 318 in response to an operation signal from the UP switch 6a. As a result, the amplification factor of the echo signal input to the A/D converter 318 is increased, whereby the amplitude of the A-mode waveform W is increased.

On the other hand, when the amplitude of the A-mode waveform W is too large (such as when saturated), the examiner operates the DOWN switch 6b. The control section 80 decreases the gain in the amplifier 318 in response to an operation signal from the DOWN switch 6b. As a result, the amplification factor of the echo signal input to the A/D converter 318 is decreased, whereby the amplitude of the A-mode waveform W is decreased.

Gate Adjustment

When the waveform of the retinal echo is unclear due to the influence of opacity, or when a superfluous echo is observed on the A-mode waveform due to an intraocular lens or the like, the examiner operates the rotating knob 5a to change the retinal detection gate. As the rotating knob 5a is rotated in a clockwise direction, the control section 80 drives the arrow G in the deeper direction of the eye (right direction). As the rotating knob 5a is rotated in a counterclockwise direction, the control section 80 drives the arrow G in the shallower direction of the eye (left direction).

The examiner aligns the detection gate G at immediately before an echo signal that is thought to be an actual retinal echo. On the basis of the modified position of the detection gate G, the control section 80 sets the nearest echo signal in the back of the detection gate G (in the deeper direction of the eye) as the retinal echo. The control section 80 further modifies the measurement value by using the set retinal echo as the measurement end point.

After the desired waveform is obtained, the examiner presses the measurement start switch. 5b, the freeze switch F on the monitor 9, or the foot switch 400. In response to the operation signal, the control section 80 starts measuring. The control section 80, on the basis of the echo information stored in the sampling memory 316, calculates measurement data. The control section 80 displays the calculated measurement data (such as measurement values) on the monitor 9 (see "M" in FIG. 3). When the measurement start switch 5b, the freeze switch F on the monitor 9, or the foot switch 400 is pressed a plurality of times, the control section 80 implements measuring in response to the respective operation signal, and displays the list M indicating each measurement result (such as measurement values) from the plurality of times (such as 10 times) of A-mode measurements on the right side of the screen. When the measurement data is acquired and displayed, the control section 80 may calculate the measurement data successively based on successively detected echo information, take in the measurement data when the operation signal is output, and displays the measurement data on the monitor 9.

By measuring the ocular axial length by using ultrasonic waves as described above, a highly reliable measurement result can be obtained even in the case of a cataract eye without the special influence of the cataract. Further, by configuring the operation system as described above, the ocular axial length can be measured in simple configuration and without detracting from operability even in the case of the apparatus configuration in which the ultrasonic probe 302 is attached to the optical interference type ocular axial length measurement apparatus.

As one of the aforementioned embodiments, the configuration in which the rotating knob 5a is used for changing the gate position in the second mode (the ocular axial length measurement mode) and the configuration in which the up/down switch 6 is used for adjusting the gain have been described. In addition, the control section 80 may utilize an operation signal from the touchscreen disposed on the monitor 9 for gate position modification or gain adjustment.

In the configuration according to the foregoing embodiment, the rotating knob 5a is used for the retinal gate position adjustment. The rotating knob 5a may be used for gate position adjustment for a certain site of the eye. For example, the rotating knob 5a is used for adjusting the gate position for the control section 80 to detect the corneal anterior surface, or the anterior surface or posterior surface of the crystalline lens.

Next, an example of operation in the corneal thickness measurement mode will be described. FIGS. 4 and 5 illustrate an example of the display screen in the corneal thickness measurement mode. Generally, the control section 80 controls the apparatus as a whole so that the operation signal from the up/down switch 6 is utilized for adjusting the gain of the echo signal. The control section 80 controls the apparatus as a whole so that the operation signal from the rotating knob 5a is used for selecting a measurement point. The control section 80 controls the apparatus as a whole so that the operation signal from the measurement start switch 5b is utilized for starting transmission and reception of ultrasonic waves by the ultrasonic probe 302 and acquiring a measurement value.

The control section 80, when measuring the corneal thickness by using the ultrasonic probe 302, displays on the monitor 9 a map C indicating a plurality of measurement points on the cornea, and a selection display (see "B" in FIGS. 4 and 5) indicating the current measurement position on the map C. The control section 80, on the basis of the operation signal input from the rotating knob 5a, changes the measurement point selected as the current measurement position. The control section 80, on the basis of the operation signal input from the up/down switch 6, adjusts the gain of the signal detected by the ultrasonic probe 302.

The control section 80 starts transmission and reception of ultrasonic waves by the ultrasonic probe 302 in response to the operation signal from the measurement start switch 5b. The control section 80, in response to the operation signal from the measurement start switch 5b after the start of transmission and reception of ultrasonic waves, acquires length information based on the signal detected by the ultrasonic probe 302, and displays the acquired length information on the monitor.

The examiner, while holding the probe 302 with one hand, contacts the end of the probe 302 onto the cornea. Further, the examiner operates the measurement start switch 5b and the up/down switch 6 with the other hand. When the measurement point selected position is modified, the examiner operates the rotating knob 5a after separating the end of the probe 302 from the cornea. Thereafter, the examiner places the end of the probe 302 on the cornea with respect to a different measurement point.

The control section 80 displays the corneal thickness map C indicating the plurality of measurement points on the left side of the monitor 9. The corneal thickness map C is a two-dimensional map with the center of the cornea located at the center, for example. The type of the map C may be modified as needed, and may include a square map or a radial map with the cornea at the center. The number of the measurement points in each map may be selected from any plural numbers.

Referring to FIG. 4, the map C is disposed radially about the cornea center. At each measurement point, the direction and distance with respect to the cornea center represent the direction and distance with respect to the cornea center of the eye E. Portions C1 to C9 indicated by solid lines are the portions set as the measurement points. Portions indicated by dotted lines are the portions not set as the measurement points.

The measurement point enclosed by a rectangle B indicates the measurement point (selected position) selected as the current measurement position from the plurality of measurement points C1 to C9. In the initial stage, the measurement point C1 corresponding to the cornea center is selected in advance. The examiner, after performing topical anesthesia on the eye E, contacts the end of the probe 302 onto the cornea center of the eye E. The examiner, in order to obtain an echo signal from the eye E, presses the measurement start switch 5b.

The control section 80 controls the operation of the probe 302 by using a signal from the measurement start switch 5b as a trigger. The control section 80, in order to receive a reflected wave from the eye E with the transducer 312, irradiates the eye E with ultrasonic waves from the transducer 312.

The control section 80 displays the waveform of the echo signal detected by the probe 302 (A-mode waveform W) on the monitor 9 (see FIG. 4). On the monitor 9, a currently set gain is displayed as a numerical value. The numerical value is increased or decreased in response to an increase or decrease of the gain.

Gain Adjustment

The examiner operates the up/down switch 6 while adjusting the position and angle of the probe 2 in order to obtain a desired waveform. The increasing and decreasing of the gain based on the operation signal from the up/down switch 6 is similar to the case of the ocular axial length measurement mode (A-mode). Thus, a detailed description will be omitted.

After the desired waveform is obtained, the examiner presses the measurement start switch 5b, the freeze switch F on the monitor 9, or the foot switch 400. In response to the operation signal, the control section 80 starts measurement. The control section 80 calculates measurement data based on the echo information stored in the sampling memory 316. The control section 80 displays the calculated measurement data on the monitor 9 (see "M" in FIG. 4). When the measurement result at the selected position is obtained, the control section 80 displays a measurement value at the selected measurement point (measurement point C1). Further, the examiner stores the measurement value in the memory 85 as a corneal thickness value at the selected position (measurement point C1). When the measurement start switch 5b, the freeze switch F on the monitor 9, or the foot switch 400 is pressed a plurality of times, the control section 80 implements measurement in response to each operation signal. The control section 80 displays the list M indicating each measurement result (such as measurement values) of a plurality of times (such as 10 times) of corneal thickness measurements on the right side of the screen. When the corneal thickness is acquired and displayed, the control section 80 may successively calculate the corneal thickness based on successively detected echo information, take in the corneal thickness when the operation signal is outputted, and display the corneal thickness on the monitor 9.

Modification of Measurement Point

FIG. 5 illustrates an example of the screen display in a state in which the selected position has been modified. After the measurement at the cornea center is completed, the examiner operates the rotating knob 5a in order to change the selected position. The control section 80 changes the measurement point that is set as the selected position from among the plurality of measurement points C1 to C9 as the rotating knob 5a is rotated. The control section 80 encloses the measurement point corresponding to the modified selected position with the rectangle B.

When the rotating knob 5a is rotated in the clockwise direction, the selected position among the plurality of measurement points C1 to C9 is successively modified in the clockwise direction. When the rotating knob 5a is rotated in the counterclockwise direction, the selected position is successively modified in the counterclockwise direction. In response to the modification of the current measurement point, the rectangle B is moved among the measurement points C1 to C9.

As illustrated in FIG. 5, after the measurement point C2 is selected, the examiner contacts the end of the probe 302 onto a cornea site at an upper-left, corner with respect to the cornea center of the eye E. After the desired waveform is obtained, the examiner presses the measurement start switch 5b, the freeze switch F on the monitor 9, or the foot switch 400. In response to the operation signal, the control section 80 measures the corneal thickness based on the echo information output, from the probe 302. Based on the measured corneal thickness, the control section 80 displays the calculated measurement data (such as a measurement value) on the monitor 9. For example, the control section 80 displays the measurement value at the measurement point C2 on the map. Further, the examiner stores the measurement value in the memory 85 as the corneal thickness value at the selected position (measurement point C2).

In response to the operation of the rotating knob 5a by the examiner, the control section 80 successively changes the measurement point selected as the selected position from among the measurement points C1 to C9. The control section 80 stores the corneal thickness at each of the successively selected measurement points in the memory 75. Thus, the control section 80 gains corneal thickness distribution information. After the corneal thickness measurement at the measurement points C1 to C9 is completed, the control section 80 ends the measurement of the corneal thickness distribution. The control section 80 displays the map M including the measurement result at each measurement point on the monitor 9.

Thus, by measuring the corneal thickness by using ultrasonic waves, even in the case of the cataract eye, a highly reliable measurement result can be obtained without the special influence of the cataract eye. Further, by configuring the operation system as described above, even in the case of the apparatus configuration in which the ultrasonic probe 302 is attached to the optical interference type ocular axial length measurement apparatus, the configuration can be simplified and the corneal thickness can be measured without detracting from operability.

As an example of the embodiment, the configuration in which the rotating knob 5a is used for changing the measurement point in the second mode (corneal thickness measurement mode), and the configuration in which the up/down switch 6 is used for gain adjustment have been described. In addition, the control section 80 may utilize an operation signal from the touchscreen disposed on the monitor 9 for measurement point modification or gain adjustment.

In an example of the embodiment, the control section 80 started the measuring by using the operation signal from the measurement start switch 5b, the freeze switch F on the monitor 9, or the foot switch 400 as a trigger. However, the embodiment is not limited to such an example, and the control section 80 may automatically start the measurement when the amplitude of the echo signal has exceeded a preset allowable level. The control section 80 may take in the measurement data successively until the values are stabilized over a plurality of times of measurements and the values for a prescribed number of times of measurement are obtained.

DESCRIPTION OF REFERENCE SIGNS

Figure 1:
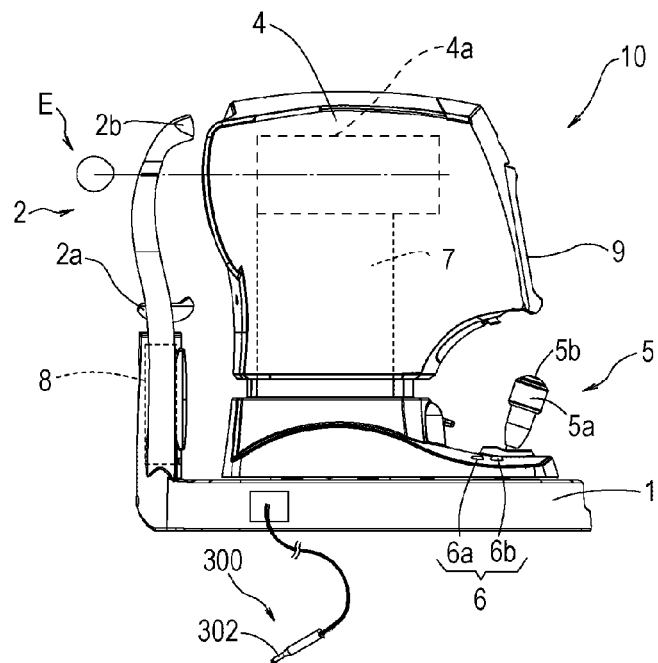
FIG. 1 is a diagram illustrating an exterior configuration of an ocular axial length measurement apparatus according to an embodiment.
Figure 2:
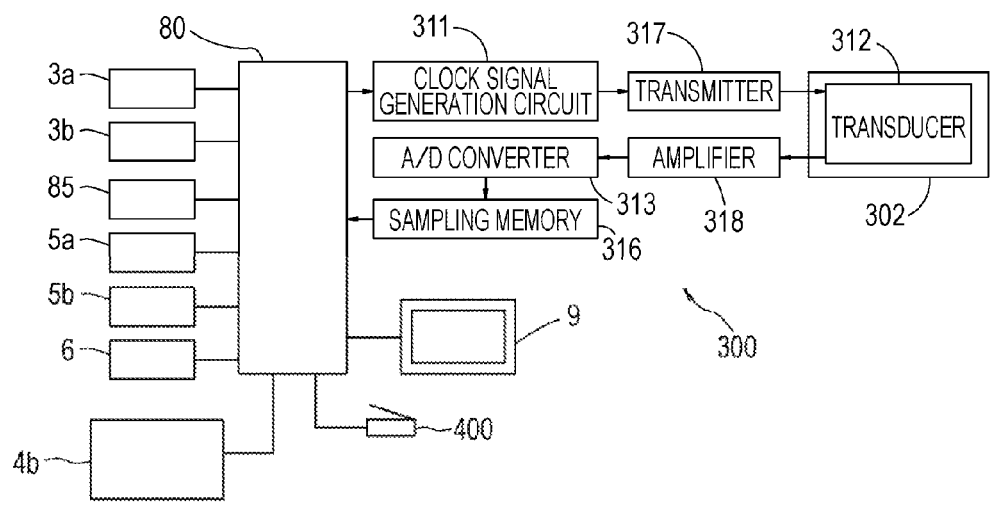
FIG. 2 is a control block diagram illustrating the ocular axial length measurement apparatus according to the embodiment.
Figure 3:
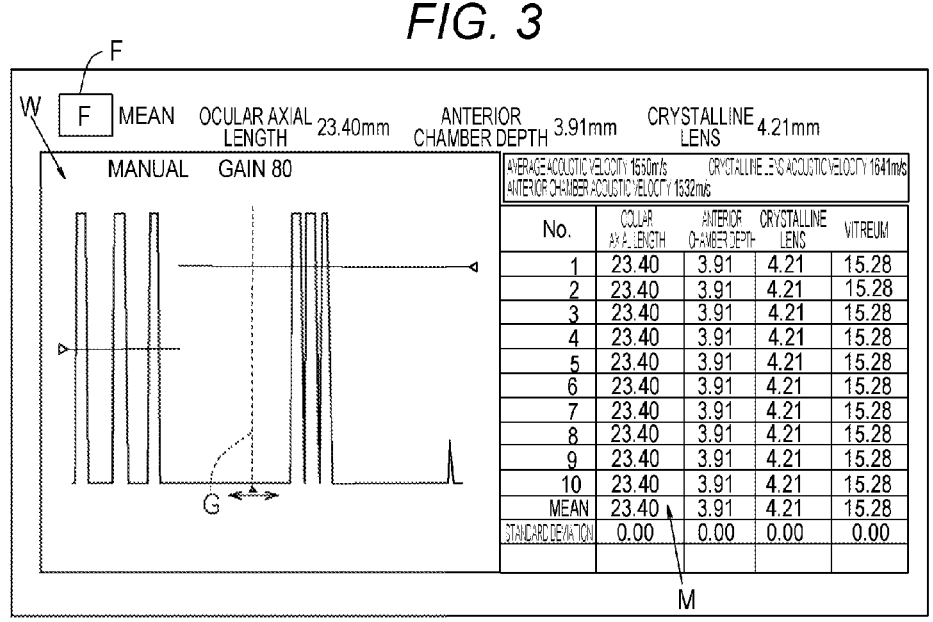
FIG. 3 is a diagram illustrating an example of a display screen in an ocular axial length measurement mode.
Figure 4:
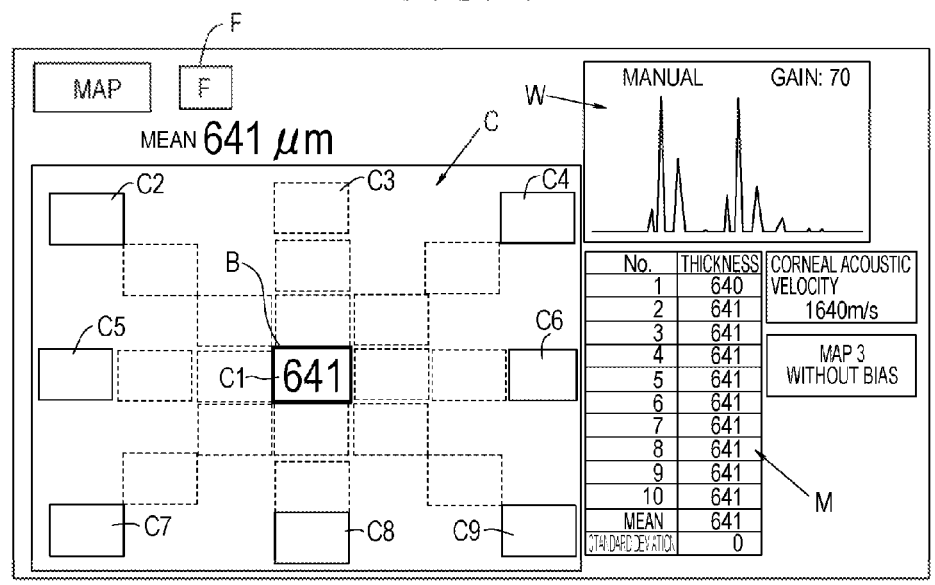
FIG. 4 is a diagram illustrating an example of the display screen in a corneal thickness measurement mode.
Figure 5:
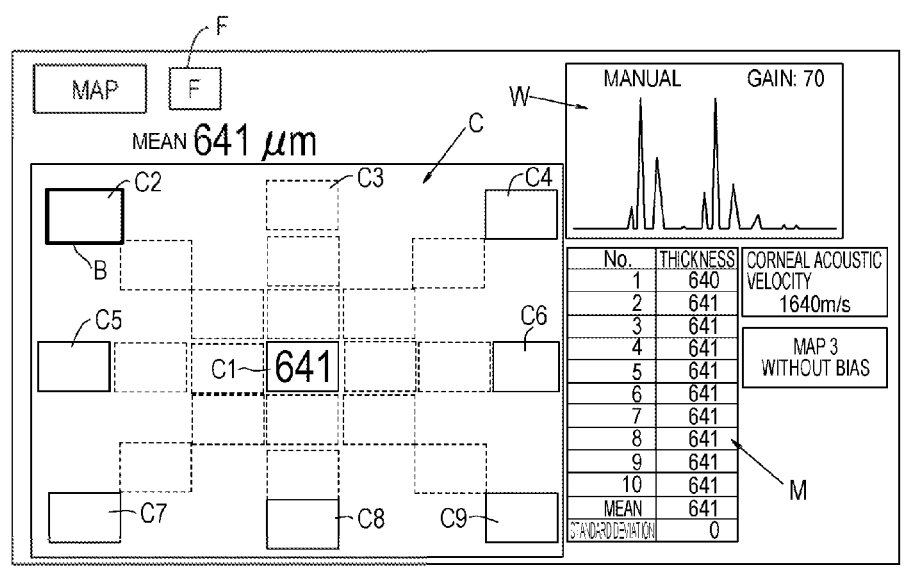
FIG. 5 is a diagram illustrating an example of the display screen in the corneal thickness measurement mode.

4 Measurement unit
4a Measuring optical system
5 Joystick
5a Rotating knob
5b Measurement start switch
6 Up/down switch
7 First drive section
8 Second drive section
80 Control section
302 Ultrasonic probe

The invention claimed is:

1. An ocular axial length measurement apparatus comprising:
a measurement unit including a measuring optical system with an optical interferometer for optically measuring the ocular axial length of an examinee's eye in a contactless manner, and an imaging optical system for capturing an anterior segment observation image;
a drive mechanism for adjusting the relative positions of the measurement unit and the examinee's eye;
an operation section operated by an examiner so as to drive the drive mechanism or the measurement unit;
a monitor capable of displaying the anterior segment observation image; and
a controller that controls the measurement unit and the driving of the drive mechanism based on an operation signal output from the operation section,
an ultrasonic probe for obtaining length information in an axial direction of the examinee's eye mounted or attached via a cable to the apparatus; and
a mode switch that switches a measurement mode of the apparatus between a measurement with the optical interferometer and a measurement with the ultrasonic probe, wherein
the controller displays on the monitor a reception waveform of an echo signal detected by the ultrasonic probe and a gate target indicating a gate position corresponding to a predetermined site with respect to the reception waveform;
when the measurement with the optical interferometer is selected by the mode switch, the controller moves the measurement unit based on an operation signal from the operation section; and
when the measurement with the ultrasonic probe is selected by the mode switch, the controller adjusts the gate position with respect to the reception waveform based on an operation signal from the operation section.

2. The ocular axial length measurement apparatus according to claim 1, wherein
the drive mechanism includes a first drive mechanism for driving the measurement unit in a vertical direction; and
the operation section is a rotating knob operated by the examiner to drive the measurement unit in the vertical direction by the first drive mechanism.

3. The ocular axial length measurement apparatus according to claim 2, wherein
the ultrasonic probe is an ultrasonic probe for A-mode.

4. The ocular axial length measurement apparatus according to claim 2, wherein
the controller changes the gate position on the monitor based on the operation signal input from the rotating knob; and the controller identifies an echo signal corresponding to a predetermined site based on the modified gate position.

5. The ocular axial length measurement apparatus according to claim 2, wherein
the ultrasonic probe is an ultrasonic probe for a pachymetry mode; and
the controller displays on the monitor both a map indicating a plurality of measurement points on the cornea and a selection display indicating a current measurement position on the map, and
the controller changes the position of the selection display on the map based on the operation signal input from the rotating knob.

6. The ocular axial length measurement apparatus according to claim 1, wherein
the drive mechanism includes a second drive mechanism for driving a chin rest in the vertical direction; and
the operation section is a chin rest switch operated by the examiner to drive the chin rest in the vertical direction by the second drive mechanism.

7. The ocular axial length measurement apparatus according to claim 1, wherein
the ultrasonic probe is an ultrasonic probe for A-mode; and
the controller adjusts the gain of a signal detected by the ultrasonic probe based on an operation signal input from the chin rest switch.

8. The ocular axial length measurement apparatus according to claim 1, wherein
the ultrasonic probe is an ultrasonic probe for a pachymetry mode;
the controller displays on the monitor both a map indicating a plurality of measurement points on the cornea, and a selection display indicating a current measurement position on the map, and
the controller adjusts the gain of a signal detected by the ultrasonic probe based on an operation signal input from the chin rest switch.

9. The ocular axial length measurement apparatus according to claim 1, comprising:
a measurement start switch operated by the examiner to input a trigger signal for starting measuring in the measurement unit, wherein
the controller starts transmission and reception of ultrasonic waves by the ultrasonic probe in response to the trigger signal input from the measurement start switch.

10. The ocular axial length measurement apparatus according to claim 1, comprising:
a start switch operated by the examiner to input a trigger signal for starting measuring in the measurement unit, wherein
the controller, after the start of transmission and reception of ultrasonic waves, acquires length information based on a signal detected by the ultrasonic probe in response to the trigger signal input from the start switch, and
the controller displays the acquired length information on the monitor.

11. The ocular axial length measurement apparatus according to claim 1, wherein
the monitor includes a touchscreen; and
the controller adjusts a gate position with respect to a reception waveform based on an operation signal input from the touchscreen.

12. The ocular axial length measurement apparatus according to claim 1, wherein
the monitor includes a touchscreen; and
the controller adjusts the gain of a signal detected by the ultrasonic probe based on an operation signal input from the touchscreen.

13. The ocular axial length measurement apparatus according to claim 5, wherein
the monitor includes a touchscreen; and
the controller, based on an operation signal input from the touchscreen, changes the position of a selection display on the map and adjusts the gain of a signal detected by the ultrasonic probe.

14. The ocular axial length measurement apparatus according to claim 7, wherein the controller displays a numerical value of the adjusted gain on the monitor.

15. The ocular axial length measurement apparatus according to claim 1, wherein
the drive mechanism includes a first drive mechanism that drives the measurement unit in a vertical direction and a second drive mechanism that drives a chin rest in the vertical direction;
the operation section includes a first operation section and a second operation section;
when the measurement with the optical interferometer is selected by the mode switch, the first operation section sends an operation signal to the controller and moves the measurement unit, and the second operation section sends an operation signal to the controller and moves the chin rest; and
when the measurement with the ultrasonic probe is selected by the mode switch, the first operation section sends an operation signal to the controller and adjusts the gate position with respect to the reception waveform, and the second operation section sends an operation signal to the controller and adjusts a gain of the echo signal detected by the ultrasonic probe.

16. The ocular axial length measurement apparatus according to claim 1, wherein
the drive mechanism includes a first drive mechanism that drives the measurement unit in a vertical direction and a second drive mechanism that drives a chin rest in the vertical direction;
the operation section includes a first operation section and a second operation section, the first operation section being a rotting knob and the second operation section being an up-down switch, a touchscreen, or combination thereof;
when the measurement with the optical interferometer is selected by the mode switch, the first operation section sends an operation signal to the controller and moves the measurement unit, and the second operation section sends an operation signal to the controller and moves the chin rest; and
when the measurement with the ultrasonic probe is selected by the mode switch, the first operation section sends an operation signal to the controller and adjusts the gate position with respect to the reception waveform, and the second operation section sends an operation signal to the controller and adjusts a gain of the echo signal detected by the ultrasonic probe.

17. An ocular axial length measurement apparatus comprising:
a measurement unit including a measuring optical system with an optical interferometer for optically measuring the ocular axial length of an examinee's eye, and an imaging optical system for capturing an anterior segment observation image;
an ultrasonic probe that detects an echo signal for obtaining length information in an axial direction of the examinee's eye;
an amplifier that amplifies the echo signal;

a first drive mechanism that drives the measurement unit in a vertical direction and a second drive mechanism that drives a chin rest in the vertical direction for adjusting relative positions of the measurement unit and the examinee's eye;

a first operation section and a second operation section that output operation signals, the first operation section being a rotting knob and the second operation section being an up-down switch, a touchscreen, or combination thereof;

a monitor that displays the anterior segment observation image;

a controller that controls the measurement unit and the first and second drive mechanisms based on the operation signals from the first and second operation sections; and a mode switch that switches a measurement mode of the apparatus between a measurement with the optical interferometer and a measurement with the ultrasonic probe, wherein the controller displays on the monitor a reception waveform of the echo signal detected by the ultrasonic probe and a gate target indicating a gate position corresponding to a predetermined site with respect to the reception waveform;

when the measurement with the optical interferometer is selected by the mode switch, the first operation section sends an operation signal to the controller and moves the measurement unit, and the second operation section sends an operation signal to the controller and moves the chin rest; and when the measurement with the ultrasonic probe is selected by the mode switch, the first operation section sends an operation signal to the controller and adjusts the gate position with respect to the reception waveform, and the second operation section sends an operation signal to the controller and adjusts a gain of the amplifier.

* * * * *